United States Patent
Selvin et al.

(10) Patent No.: US 8,445,867 B2
(45) Date of Patent: May 21, 2013

(54) PHOTOBLEACHING AND INTERMITTENCY LOCALIZATION MICROSCOPY

(75) Inventors: Paul R. Selvin, Urbana, IL (US); Paul Dennis Simonson, Savoy, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/578,218

(22) PCT Filed: Feb. 22, 2011

(86) PCT No.: PCT/US2011/025750
§ 371 (c)(1),
(2), (4) Date: Aug. 9, 2012

(87) PCT Pub. No.: WO2011/106323
PCT Pub. Date: Sep. 1, 2011

(65) Prior Publication Data
US 2012/0313012 A1    Dec. 13, 2012

Related U.S. Application Data

(60) Provisional application No. 61/307,440, filed on Feb. 23, 2010.

(51) Int. Cl.
*G01J 1/58*    (2006.01)

(52) U.S. Cl.
USPC .................................. 250/458.1; 250/459.1

(58) Field of Classification Search
USPC .......................................... 250/458.1, 459.1
See application file for complete search history.

(56) References Cited

U.S. PATENT DOCUMENTS

| | | | | |
|---|---|---|---|---|
| 5,485,530 | A * | 1/1996 | Lakowicz et al. | 382/191 |
| 7,557,915 | B2 * | 7/2009 | Maier et al. | 356/301 |
| 2007/0083124 | A1 * | 4/2007 | Ehben et al. | 600/476 |
| 2009/0045353 | A1 * | 2/2009 | Alexeevich et al. | 250/482.1 |

* cited by examiner

Primary Examiner — Mark R Gaworecki
(74) Attorney, Agent, or Firm — Richard Aron Osman

(57) ABSTRACT

A method of image analysis creates super-resolution images from images with high densities of fluorophores by processing a movie in which the fluorescent molecules or particles are photobleaching or blinking. The method looks for the individual photobleaching events that can be located with high resolution (nm to tens of nanometers scale). The positions of the photobleaching or blinking events are then drawn in a composite image that is at a much higher resolution than the original fluorescence movie.

10 Claims, 6 Drawing Sheets

PHOTOBLEACHING AND INTERMITTENCY LOCALIZATION MICROSCOPY

This application is a U.S. national filing of Ser No. PCT/US11/25750, filed Feb. 22, 2011, which claims priority to U.S. Ser. No. 61/307,440, filed Feb. 23, 2010.

FIELD OF THE INVENTION

The field of the invention is photobleaching and intermittency localization microscopy.

BACKGROUND OF THE INVENTION

Using highly sensitive CCD cameras, single fluorescent molecules can be detected and imaged as fluorescent spots (in the absence of background fluorescence). Fitting a single fluorophore such that its center can be located to nanometer accuracy has enabled "super resolution" microscopy, i.e., resolution much better than 200-300 nm accuracy. Using photoswitchable fluorophores (via PALM [1] or STORM [2, 3]) or by forcing dyes into long-lived dark states (via dSTORM [4]), individual fluorophores are visible, even when fluorophore density is high. Because the individual fluorophores are visible and can be fit to two-dimensional Gaussian functions, the positions of the fluorophores can be localized to nanometer accuracy (5, 6). The positions of the individual fluorophores can then be used to draw a composite super-resolution image.

Here we show that it is unnecessary to see single spots to achieve super-resolution imaging. Fluorophores stochastically photobleach when exposed to laser excitation. Resulting quantized drops in fluorescence intensity can be localized, even with background, to create super-resolution images from standard photobleaching movies. This is achieved by subtracting post-photobleaching images from pre-photobleaching images. In addition, we use frame averaging and weighted two-dimensional Gaussian fitting to reduce the effects of shot noise that are inherent in the higher fluorescent background. In an analogous way, we can also localize fluorophores that blink, transitioning from dark to bright states, and vice versa. This technique thus presents a much simpler way to create super resolution images. We are calling our technique "photobleaching and intermittency localization microscopy," or PhILM for short.

SUMMARY OF THE INVENTION

In one aspect the invention provides a method of photobleaching and intermittency localization microscopy ("PhILM"), the method comprising steps:

a) processing a movie of fluorophores transitioning between fluorescent and dark states by sequentially subtracting frame (n+1) from frame n to get frame n', frame n from frame (n−1) to get frame (n−1)', etc. to obtain a "backwards-subtracted movie" comprising frames 1', 2', . . . , (n−1)', n', (n+1)', etc.;

b) detecting in the backwards-subtracted movie dark and bright spots, wherein bright spots correspond to transitions from fluorescing-states-to-dark-states ("photobleaching" events), and dark spots correspond to transitions from dark-states-to-fluorescing-states ("blinking" events) and storing corresponding frame numbers and positions of these photobleaching or blinking events;

c) localizing positions of the fluorophore transition events with sub-pixel resolution; and d) creating a high resolution image by plotting the positions of the localized fluorophore transition events in a final image.

In particular embodiments the localizing step is performed by two-dimensional Gaussian fitting, Airy disc fitting, centroid fitting, fluoroBancroft algorithm, or wavelet segmentation.

In another aspect the invention provides a method of photobleaching and intermittency localization microscopy ("PhILM"), the method comprising steps:

a) processing a movie of fluorophores transitioning between fluorescent and dark states by sequentially subtracting frame (n−1) from frame n to get frame n', frame n from frame (n+1) to get frame (n+1)', etc. to obtain a "forward-subtracted movie" comprising frames 1', 2', . . . , (n−1)', n', (n+1)', etc.;

b) detecting in the forward-subtracted movie dark and bright spots, wherein dark spots correspond to transitions from fluorescing-states-to-dark-states ("photobleaching" events), and bright spots correspond to transitions from dark-states-to-fluorescing-states ("blinking" events) and storing corresponding frame numbers and positions of these photobleaching or blinking events;

c) localizing positions of the fluorophore transition events with sub-pixel resolution; and d) creating a high resolution image by plotting the positions of the localized fluorophore transition events in a final image.

In particular embodiments the localizing step is performed by two-dimensional Gaussian fitting, Airy disc fitting, centroid fitting, fluoroBancroft algorithm, or wavelet segmentation.

In another aspect the invention provides a method of photobleaching and intermittency localization microscopy ("PhILM"), the method comprising steps:

a) processing a movie of fluorophores transitioning between fluorescent and dark states by sequentially subtracting frame (n+1) from frame n to get frame n', frame n from frame (n−1) to get frame (n−1)', etc. to obtain a "backwards-subtracted movie" comprising frames 1', 2', . . . , (n−1)', n', (n+1)', etc.;

b) detecting in the backwards-subtracted movie dark and bright spots using a spot detection algorithm, wherein bright spots correspond to transitions from fluorescing-states-to-dark-states ("photobleaching" events), and dark spots correspond to transitions from dark-states-to-fluorescing-states ("blinking" events) and storing corresponding frame numbers and positions of these photobleaching or blinking events;

c) calculating a maximum number of frames that can be averaged before a transition event and after a transition event, for each spot, by comparing the spot's position and frame number with the other spots' positions and frame numbers to obtain frame ranges, wherein consecutive frames before and after the event are averaged as long as another event does not occur within a certain minimum radius of the event of interest, within the frames to be averaged;

d) averaging frames before each spot using the frame ranges calculated in step c) to produce a "pre-event averaged image" and averaging frames after each spot using the frame ranges calculated in step c) to produce a "post-event averaged image";

e) subtracting for each photobleaching event the post-event averaged image from the pre-event averaged image to produce a corresponding "fitting image", or subtracting for each blinking event the pre-event averaged image from the post-event averaged image to produce a corresponding "fitting image";

f) localizing in the fitting image positions of the fluorophore transition events with sub-pixel resolution to find the best estimate of the position of the center of the fluorophore; and g) creating from the best estimates of the positions of the fluorophores calculated in step f) a high resolution image by plotting the positions of all the localized fluorophore transition events in a final image, wherein events that are not fit by a Gaussian function in step f) are not plotted in the final image.

In particular embodiments the localizing step is performed by two-dimensional Gaussian fitting, Airy disc fitting, centroid fitting, fluoroBancroft algorithm, or wavelet segmentation.

In particular embodiments the localizing step is performed by fitting the fitting image for each photobleaching or blinking event to a two-dimensional Gaussian function, using the pixels within a determined radius of the photobleaching or blinking event, to find the best estimate of the position of the center of the fluorophore.

In another aspect the invention provides a method of photobleaching and intermittency localization microscopy ("PhILM"), the method comprising steps:

a) processing a movie of fluorophores transitioning between fluorescent and dark states by sequentially subtracting frame (n−1) from frame n to get frame n', frame n from frame (n+1) to get frame (n+1)', etc. to obtain a "forward-subtracted movie" comprising frames 1', 2', . . . , (n−1)', n', (n+1)', etc.;

b) detecting in the forward-subtracted movie dark and bright spots using a spot detection algorithm, wherein dark spots correspond to transitions from fluorescing-states-to-dark-states ("photobleaching" events), and bright spots correspond to transitions from dark-states-to-fluorescing-states ("blinking" events) and storing corresponding frame numbers and positions of these photobleaching or blinking events;

c) calculating a maximum number of frames that can be averaged before a transition event and after a transition event, for each spot, by comparing the spot's position and frame number with the other spots' positions and frame numbers to obtain frame ranges, wherein consecutive frames before and after the event are averaged as long as another event does not occur within a certain minimum radius of the event of interest, within the frames to be averaged;

d) averaging frames before each spot using the frame ranges calculated in step c) to produce a "pre-event averaged image" and averaging frames after each spot using the frame ranges calculated in step c) to produce a "post-event averaged image";

e) subtracting for each photobleaching event the post-event averaged image from the pre-event averaged image to produce a corresponding "fitting image", or subtracting for each blinking event the pre-event averaged image from the post-event averaged image to produce a corresponding "fitting image";

f) localizing in the fitting image positions of the fluorophore transition events with sub-pixel resolution to find the best estimate of the position of the center of the fluorophore; and g) creating from the best estimates of the positions of the fluorophores calculated in step f) a high resolution image by plotting the positions of all the localized fluorophore transition events in a final image, wherein events that are not fit by a Gaussian function in step f) are not plotted in the final image.

In particular embodiments the localizing step is performed by two-dimensional Gaussian fitting, Airy disc fitting, centroid fitting, fluoroBancroft algorithm, or wavelet segmentation.

In particular embodiments the localizing step is performed by fitting the fitting image for each photobleaching or blinking event to a two-dimensional Gaussian function, using the pixels within a determined radius of the photobleaching or blinking event, to find the best estimate of the position of the center of the fluorophore.

DETAILED DESCRIPTION OF SPECIFIC EMBODIMENTS OF THE INVENTION

Figure 1:
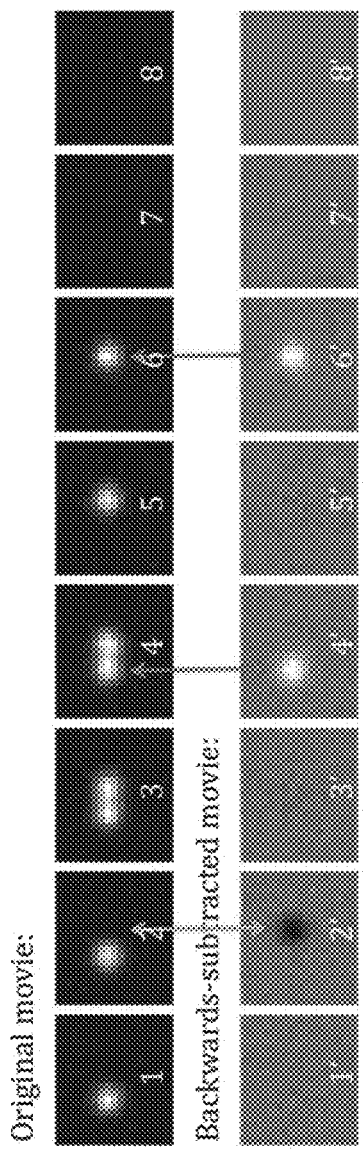
FIG. 1. Creating the backwards-subtracted movie: frame 8 of the original movie is subtracted from frame 7 to get 7' of the backwards-subtracted movie; frame 7 is subtracted from frame 6 to get 6', etc.

The invention provides methods, compositions, apparatuses, systems, software, hardware, instrumentation and kits for photobleaching and intermittency localization microscopy (PhILM). In one embodiment, the method comprises the following steps:

a) A movie of fluorophores transitioning from fluorescent to dark states (e.g. photobleaching) or from dark states to fluorescing states (e.g. as in blinking) is processed by sequentially subtracting frame (n+1) from frame n to get frame n', frame n from frame (n−1) to get frame (n−1)', etc. The output is a new "backwards-subtracted" movie composed of frames 1', 2', . . . , (n−1)', n', (n+1)', . . .

b) The "backwards-subtracted" movie is inspected for dark and bright spots using a spot detection algorithm. Bright spots correspond to transitions-from-fluorescing-states-to-dark-states (hereafter referred to as "photobleaching") events, and dark spots correspond to transitions-from-dark-states-to-fluorescing-states (hereafter referred to as "blinking") events. The frames (times) and positions of these photobleaching or blinking events are stored for use in step c).

c) The maximum number of frames that can be averaged before a transition event and after a transition event, for each spot, is calculated by comparing the spot's position and frame number with the other spots' positions and frame numbers. Consecutive frames before and after the event can be averaged as long as another event does not occur within a certain minimum radius of the event of interest, within the frames to be averaged.

d) For each spot, which represents a photobleaching or blinking event, the frames before the event are averaged using the frame ranges calculated in step c) to produce the "pre-event averaged image." Similarly, the frames after the event are averaged to produce the "post-event averaged image."

e) For photobleaching events, the post-event averaged image is subtracted from the pre-event averaged image to produce the "fitting image." For blinking events, the pre-event averaged image is subtracted from the post-event averaged image to produce the fitting image.

f) The resulting fitting image for each photobleaching or blinking event is fit to a two-dimensional Gaussian function, using the pixels within a certain radius of the photobleaching or blinking event, to find the best estimate of the position of the center of the fluorophore.

g) The best estimates of the positions of the fluorophores calculated in step f) are used to create a high resolution image by plotting the positions of all the localized fluorophore transition events in the new image. Events that are not fit well by a Gaussian function in step f) are not plotted in the final image.

Of course the order of subtracting the pre and post photobleaching events from each other is essentially arbitrary: if you reverse the order and multiply the image by −1 (or you can just let your Gaussian fitter do the fitting, and it can insert a −1 when it fits it correctly), you have essentially the same image you would otherwise get.

Also, the recited steps may each be practiced in alternative ways. As examples:

Step a) may be practiced in alternative ways such as: (i) create a "forwards-subtracted" movie by subtracting frame (n−1) from frame n to get frame n', etc. In this case, dark spots correspond to photobleaching events and bright spots correspond to blinking events; (ii) and alternative methods may be substituted as long as the method identifies the times and positions of the fluorophore transition events.

Step b) may also be practiced in alternative ways such as: (i) The dark and bright spots may refer to photobleaching or blinking events, depending on whether a forwards-subtracted or backwards-subtracted movie was used.

Step c) may also be practiced in alternative ways such as: (i) Assuming that frame averaging is not necessary. In this case step c) can effectively be skipped by using only one frame before and one frame after an event in step d). Equivalently, this way amounts to fitting the spots in the backwards-subtracted movie directly (i.e., by using the movie created in step a), the work in step e) is already done).

Step f) may also be practiced in alternative ways such as: (i) Localizing the fluorophore transition event with sub-pixel resolution using methods other than two-dimensional Gaussian fitting such as fitting to an Airy disc, using the fluoroBancroft algorithm, using centroid fitting, etc. These different methods will give better or worse fitting accuracy than the two-dimensional Gaussian fitting method. In fact, a variety of suitable methods of localization of fluorescent probes are known, e.g. Hede et al. Nature Methods 6, 689-690 (2009); Sun & Andersson, Applied Physics B: Lasers and Optics Vol. 94, No. 3, 403-9 (March 2009), etc.

The subject method transforms a first movie of fluorophores transitioning from fluorescent to dark states or from dark states to fluorescing state into a forward or backwards-subtracted movie. The method then employs spot detection and fitting protocols to identify best estimates of the position of the center of the fluorophore, which are then used to create a high resolution image by plotting the positions of all the localized fluorophore transition events in the new image. As exemplified below, steps of the method may be implemented with a correspondingly programmed-computer. The method may also be practiced in conjunction with antecedent steps of generating the input movie by fluor-microscopy using a suitable microscope, camera and fluorophore.

Current methods for doing super-resolution fluorescence microscopy are rather complex for the typical biologist to apply. For example, STORM and PALM rely upon using photoswitchable pairs of fluorophores that are cycled on and off repeatedly using special laser cycling equipment. They also require, in general, two different lasers: one to make the fluorophores go from a dark to an excitable state, and a second one to make the excitable fluorophore to actually fluoresce. This equipment is not found in most biology labs, and the requirement to use photoswitchable fluorophores limits the types of fluorophores that can be used. dSTORM removes some of the restrictions (the types of dyes that can be used and laser cycling, including the use of two lasers), but necessary reagents and laser intensities can be difficult to use or optimize. We therefore desired to create a method that was less restrictive and accessible to many more biologists. By simply recording a movie of the photobleaching (or blinking) fluorescent image using a sensitive CCD camera, the movie can be processed offline to produce a super resolution image using the algorithm described below. The algorithm can also be applied to data produced using experimental methods for PALM, STORM, and dSTORM. While the other methods will ultimately yield higher resolution images, this technique can be immediately available to a much broader range of users.

Determining the times and locations of the photobleaching events. Because we wish to identify the times and positions of hundreds or thousands of individual photobleaching and blinking events on a potentially complex fluorescent background, we need a systematic, automated way to do this. This can be done by creating what we call a "backwards-subtracted movie" and localizing the resulting light and dark spots that correspond to photobleaching and transition-to-bright-state events, respectively. It could also have been done in a forwards-subtracted way, but backwards-subtracted is more intuitive for thinking about photobleaching. For frames labeled by index k, the backwards-subtracted movie is created by subtracting frame (k+1) from frame k to get new frame k', which is then inserted into the new backwards-subtracted movie. The new frame k', contains light and dark spots on a flat background (see FIG. 1). Light spots correspond to photobleaching events, i.e., there is a fluorescing molecule in frame k that is not fluorescing in frame (k+1). Dark spots indicate transition-to-bright-state events, i.e., there is a molecule that is fluorescing in frame (k+1) but not in frame k. We use a spot detection algorithm, described below, to automatically locate the dark and light spots in every frame in the backwards-subtracted movie. After doing so, the located spots can be fit to two-dimensional Gaussian functions (or similar fitting procedures—see for example [7]) directly and used to plot a super-resolution image. To improve signal-to-noise ratios, however, the information about the times and locations of the photobleaching and blinking events are used to determine over what range before and after events occur that frames can be averaged. This is done in order to reduce noise that might otherwise be more significant with no frame averaging. The frame ranges are chosen such that the frames can be averaged until a frame is encountered in which a photobleaching or blinking event occurs that is within a given radius of the position of the event of interest. This minimum separation distance is selected by the user (we generally choose six pixels as the minimum distance between events). If two events occur in the same frame and are closer than the minimum separation distance, both events are rejected and not used in creating the super-resolution image, with the caveat that both spots cannot be well fit by Gaussians because they are too close together.

FIG. 1 provides a simple example showing how photobleaching events and transition-to-bright-state events will be represented by bright and dark spots, respectively, in the backwards-subtracted movie.

Dealing with noise. While PALM, STORM, and dSTORM localize fluorophores with essentially dark backgrounds (except for dark noise contributed by the camera) because nearby fluorophores are turned off, the same is not true for the case when photobleaching or blinking fluorophores are localized on a fluorescent background. In this case, the noise is governed by (1) the dark noise due to the camera in the pre-photobleaching image, (2) the shot noise in the pre-photobleaching image, (3) the shot noise in the post-photobleaching image, (4) the dark noise in the post-photobleaching image, and (5) intrinsic fluctuations in the amount of fluorescence from the fluorophores themselves. Thus, having many fluorophores in the background will reduce the signal to noise ratio. Because one frame is subtracted from another, the standard deviations of the individual pixel intensities add in quadrature to give the total pixel noise of the resulting subtracted image (8). If several pre-photobleaching (or post-photobleaching) frames can be averaged to produce the averaged pre-photobleaching image, the noise is reduced by a factor of $\sqrt{N}$ where N is the number of frames averaged. Thus, it is advantageous, in terms of noise, to average as many of the pre- or post-photobleaching frames together as possible. The total noise associated with a single pixel in the final (subtracted) image can be estimated by $$\sigma = \sqrt{\frac{\sigma_{A,shot}^2}{N_A} + \frac{\sigma_{A,dark}^2}{N_A} + \frac{\sigma_{B,shot}^2}{N_B} + \frac{\sigma_{B,dark}^2}{N_B}}$$

where $\sigma_{A,shot}$ is the shot noise associated with the pixel in the frames after photobleaching, $\sigma_{A,dark}$ is the associated dark noise in the frames after photobleaching, and $N_A$ is the number of frames after the photobleaching event that are averaged. By replacing the A with B in these terms, the corresponding values are represented for the frames before photobleaching. In our software, we estimate $\sigma_{A,shot}$ as the square root of the pixel intensity (after subtracting the camera baseline count) of the frame-averaged image. $\sigma_{A,dark}$ is estimated by selecting a portion of the image in which there are no fluorophores present and finding the standard deviation of the pixel intensities. $\sigma_{A,dark}$ is assumed to be equal to $\sigma_{B,dark}$. Once the averaged and subtracted image is calculated, the resulting spot image can be fit to a two-dimensional Gaussian to localize the fluorophore. The Gaussian fit is done by fitting all pixels within a given radius of the brightest pixel of the spot using Levenberg-Marquardt fitting (using the GNU Scientific Library). The individual pixels are weighted according to the noise associated with each pixel. Using a weighted Gaussian fit reduced fit error by about 10% for simulated single spots on dark, uniform backgrounds—it was therefore concluded that the improvement in fitting accuracy would be improved by at least 10% for a non-uniform background. The fitting accuracy is estimated as the error reported by the fitting program using the covariance matrix of the best fit parameters, and the errors were found to be very near the fitting accuracy predicted by Thompson et al. (5) for single spots on flat backgrounds. In our applications, however, we do not estimate the error using the Thompson et al. equation but, rather, use the error reported by the fitting program since the error equation is derived by assuming a flat background with Gaussian noise.

Spot detection algorithm. While many of the existing spot detection algorithms would work well in our method, we wrote the following algorithm to automatically detect spots in the backwards-subtracted image that correspond to photobleaching events:

1. Change all pixel values that are below zero to zero. This is done so that transition-to-bright events (which appear as dark spots in the image) do not interfere with finding spots that correspond to photobleaching events.

2. To dilate the image, each pixel's intensity value is replaced with the greatest intensity value of the eight nearest neighbors, or it is unchanged if the pixel intensity is greater than that of any one of the eight nearest neighbors. The image might have to be dilated twice (i.e., apply this step twice) for very low signal to noise ratios.

3. Find the positions of all pixels that were not affected by the dilation. These are the local maxima.

4. Determine the average pixel intensity of all pixels within the radius R (generally R is chosen to be three pixels, which encloses the diffraction limited spot) of a given local maximum and call it the "spot average pixel intensity."

5. Determine the average pixel intensity of all pixels between R and R+dR (dR is generally chosen to be one pixel) around the local maximum and call it the "average local background intensity."

6. Subtract the local background intensity from the spot average pixel intensity. Call it the "background-subtracted average spot intensity."

7. Compare this with a chosen threshold value. Local maxima with values that are above the chosen threshold are considered "real" spots.

8. Perform an initial two-dimensional Gaussian fit on the spot. Reject spots that are either too narrow or too wide to be considered as reasonable spots corresponding to single molecules.

9. An output TIFF file is produced that can be compared with the original image file to check spot detection performance.

Spots corresponding to transition-to-bright-state events, which appear darker than background in the backwards-subtracted image, are detected in a very similar way:

1. Change all pixel values that are above zero to zero. This is done so that photobleaching events (which appear as bright spots in the image) do not interfere with finding spots that correspond to transition-to-bright-state events.

2. To dilate the image, each pixel's intensity value is replaced with the smallest intensity value of the eight nearest neighbors, or it is unchanged if the pixel intensity is less than that of any one of the eight nearest neighbors. The image might have to be dilated twice (i.e., apply this step twice) for very low signal to noise ratios.

3. Find the positions of all pixels that were not affected by the dilation. These are the local minima.

4. Determine the average pixel intensity of all pixels within the radius R (generally R is chosen to be three pixels, which encloses the diffraction limited spot) of a given local maximum and call it the "spot average pixel intensity."

5. Determine the average pixel intensity of all pixels between R and R+dR (dR is generally chosen to be one pixel) around the local maximum and call it the "average local background intensity."

6. Subtract the local background intensity from the spot average pixel intensity. Call it the "background-subtracted average spot intensity." Multiply by −1 to make the value positive.

7. Compare this with a chosen threshold value. Local minima with values that are above the chosen threshold are considered "real" spots.

8. Perform an initial two-dimensional Gaussian fit on the spot. Reject spots that are either too narrow or too wide to be considered as reasonable spots corresponding to single molecules.

9. An output TIFF file is produced that can be compared with the original image file to check dark spot detection performance.

Drawing the super-resolution image. A typical microscope setup that can be used for single molecule detection will include a 60-100× high NA objective, 1.5× internal microscope magnification, and a sensitive CCD array camera. The width of a single pixel in the fluorescence image will correspond to the real, physical widths of the camera pixels divided by the total magnification of the sample. For example, an Olympus microscope using a 100× objective with an additional 1.5× (total magnification is 150×) and an Andor iXon+ camera (with pixel width 16 um) will have an effective pixel size of 106.7 nm. For super resolution images, the resolution is on the order of 10-50 nm, which makes it clear that using a pixel size of 106.67 nm will not represent well the true resolution. Instead, pixel widths in the final super-resolution images are chosen to be on the order of 10 nm. The localized fluorophores are then plotted as two-dimensional Gaussian functions with widths corresponding to the localization accuracy of the fit. These widths are typically 5-10 times smaller than the width of the corresponding diffraction-limited fluorescent spots.

The algorithm is readily ported to UNIX, Macintosh, LINUX, or Windows operating systems.

Theoretical limitations. The method is limited by signal to noise ratios but also by the maximum density of fluorophores that can be permitted. There are basically three ways in which the density of fluorophores limits the technique.

First, more fluorophores means that there will be more background fluorescence. This in turn will reduce signal-to-noise and hence the fitting accuracy of the individual spots.

Second, if two (or more) fluorophores simultaneously (that is, on the order of the frame acquisition time of the camera) photobleach, and if these fluorophores are close enough such that their point spread functions cannot be separately fit by Gaussian functions, then the two photobleaching events cannot be used to construct the final super resolution image (however, if the two fluorophores are close enough in space, i.e. they are within the same diffraction-limited spot, and photobleach simultaneously, the program will not be able to tell that there are two separate fluorophores—they will be treated as one photobleaching spot, albeit with a fairly large drop in intensity). Therefore, the useful density of fluorophores is limited by the photobleaching lifetime of the individual fluorophores. The theoretical maximum density, based on these criteria, then requires that the average time between photobleaching events is long enough to fit one fluorophore per fitting area. For simulated fluorescent spot data with a width of 1.5 pixels and 700 counts peak intensity on a flat background, the spot fitting accuracy did not increase significantly past a fitting radius of 3 pixels. For fitting the real data, we therefore required photobleaching events to be at least 6 pixels apart, and we used a fitting radius of four pixels for the Gaussian fitting.

Finally, the fluorophore density is limited by the dynamic range of the CCD camera. All CCD array cameras have a maximum permissible light intensity at which the CCDs become saturated. By lowering the gain of the camera, the amount of light that can be detected without saturating the camera is increased, but the sensitivity for photons that can be detected for each fluorophore is decreased. When the camera gain is too low, the signal to noise ratio for single molecules is too low for fitting by a Gaussian function, thus rendering the fitting of individual spots with high accuracy impossible.

We note that it is difficult (except in the case of blinking quantum dots) to localize as many fluorophores as can be localized using other super-resolution techniques because fluorophores in those cases can be cycled on and off many times. However, our technique requires no special laser cycling equipment and is compatible with all fluorophores that are sufficiently bright.

We also note that background spots, such as fluorophores bound non-specifically to the coverslip surface, will tend to stand out more since fluorophores in crowded regions will not be identified as easily as those in the less crowded regions.

EXAMPLES

Example Applications

Imaging Microtubules

As a test of the improvement in resolution that can be achieved, we recorded movies of fluorophore-labeled microtubules as they photobleached and then applied our PhILM algorithm to the resulting movies. Microtubules have a diameter of 25 nm (2). The apparent width of a microtubule using conventional fluorescence microscopy, however, is governed by the diffraction limit of light, making the apparent width closer to 300 nm. We began by using microtubules labeled with rhodamine. The starting labeling density was approximately 4:1 unlabeled:labeled tubulin (Cytoskeleton, Cat. No. TL238 and TL590M). The microtubules were excited using 532 nm laser excitation and total internal reflection fluorescence (TIRF) microscopy. The microtubules were imaged in a solution containing beta-mercaptoethanol (Fluka) and oxygen scavenging reagents (PCA/PCD) to improve fluorophore stability (9, 10).

Figure 2:
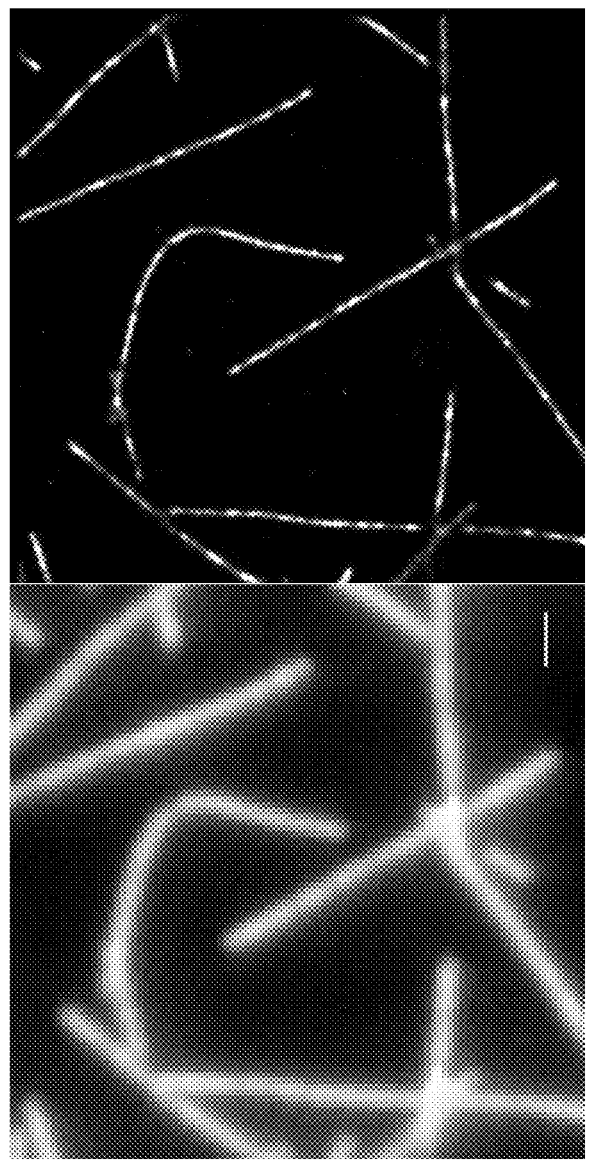
FIG. 2. Applying the technique to microtubules. Left panel: the regular TMR-fluorescence image before photobleaching (the scale bar indicates 1 um); Right panel: the resulting super-resolution image.

FIG. 2. shows application of the technique to microtubules, wherein the localized photobleaching and transition-to-bright-state events are plotted as two-dimensional Gaussians with widths equal to 2 times the fitting accuracy for the center of the corresponding spot.

To quantify the improvement in resolution, we selected short, straight microtubule segments and fit the localized spots/fluorescence intensity along the length of the microtubule to a straight line. The distribution of spots/fluorescence perpendicular to the fit line was used to calculate the widths of the microtubules in the regular and super-resolution images (see FIG. 3). We found less than 60 nm resolution and less than 100 nm resolution for TMR-labeled and GFP-kinesin-labeled microtubules, at least a five-fold improvement over conventional optical microscopy.

Figure 3:
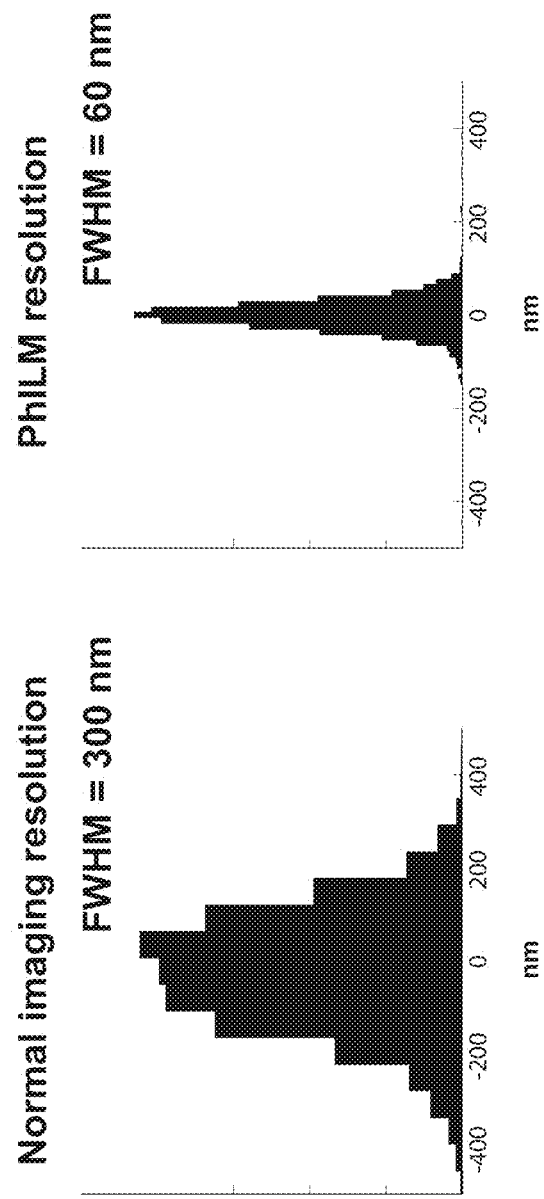
FIG. 3. Comparison between widths of microtubules observed in regular (left) and PhILM (right) images; FWHM=full width half maximum.

FIG. 3. shows a comparison between widths of microtubules observed in regular (left) and PhILM (right) images. The histogram on the left shows the intensity profile across the width of the microtubule using normal, diffraction-limited fluorescence imaging. The histogram on the right shows the distribution of localized fluorophores across the width of the microtubule in the super-resolution image.

Example Applications

Super-Resolution Images of Labeled Axonemes

Finding an improvement in resolution using microtubules is useful, but it is also instructive to know whether or not the technique can distinguish structures with different widths. Axonemes typically have a "9+2" arrangement where the circumference of the axoneme has nine "doublets" of microtubules running along the length of the axoneme, and a pair of microtubules running up the center of the axoneme (see FIG. 3). The diameter of isolated axonemes is expected to be between 160 and 200 nm, depending on the presence of Mg++ in the surrounding buffer (11), making the diameter at least six times greater than that of microtubules.

Figure 4:
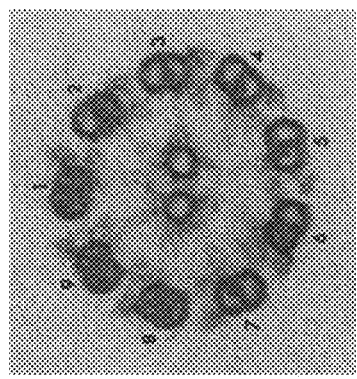
FIG. 4. Electron microscopy image of ciliary axoneme cross section.

FIG. 4 is an electron microscopy image of ciliary axoneme cross section, adapted from (11).

Because of the large diameter and the short penetration depth of excitation light into samples using TIRF microscopy, it was necessary to image axonemes conjugated with tetramethylrhodamine using epifluorescence microscopy. We found a full-width-at-half-maximum (FWHM) value of 180 nm for the axonemes (see FIG. 6), which is much larger than the value for microtubules and close to the expected value of the real axoneme diameter (160-200 nm).

Figure 5:
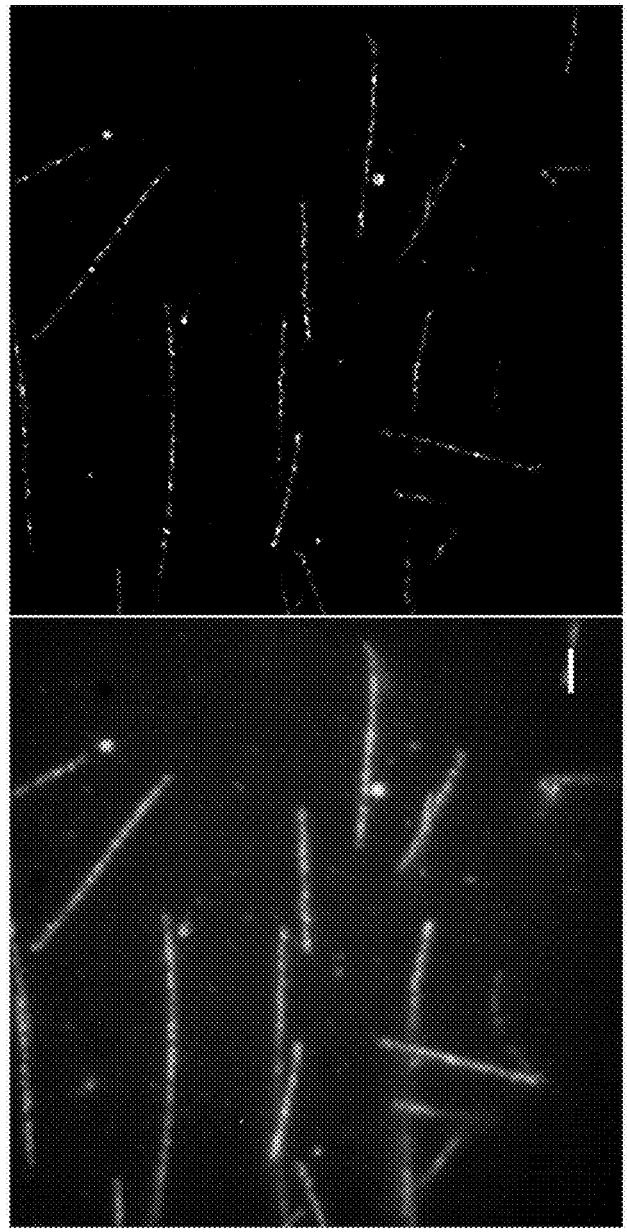
FIG. 5. Normal and super resolution images of axonemes. Left panel: The regular TMR-fluorescence image before photobleaching (the scale bar indicates 2 um); Right panel: The resulting super-resolution image.

FIG. 5 depicts normal and super resolution images of axonemes. (Left) The regular TMR-fluorescence image before photobleaching. The scale bar indicates 2 um. (Right) The resulting super-resolution image. The localized photobleaching and transition-to-bright-state events are plotted as two-dimensional Gaussians with widths equal to 2 times the fitting accuracy for the center of the corresponding spot.

Figure 6:
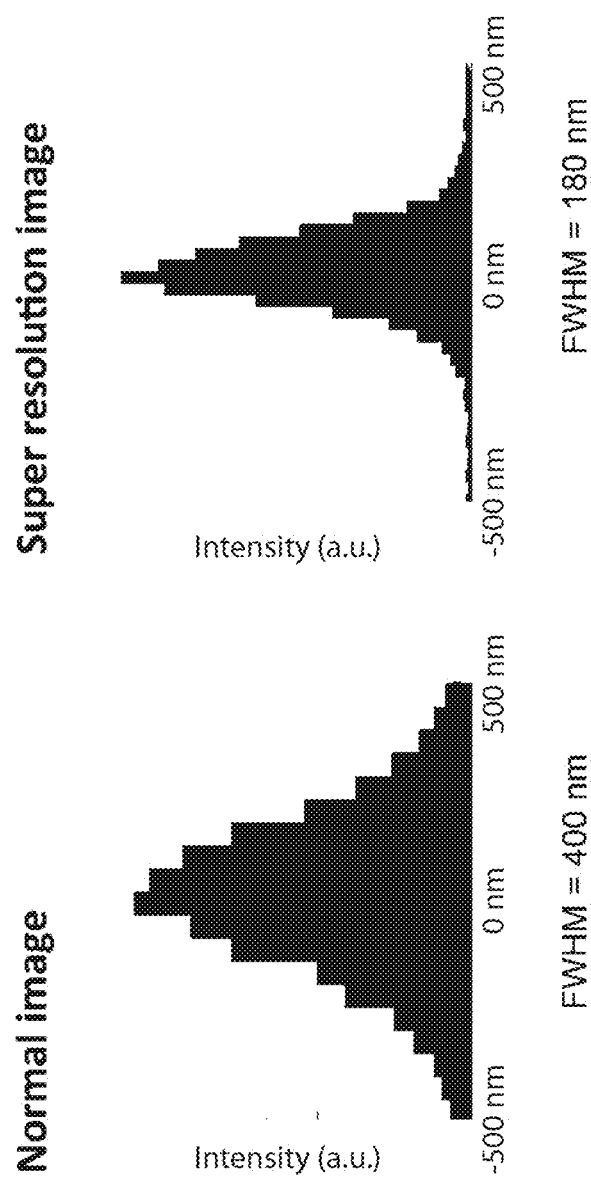
FIG. 6. Comparison between widths of axonemes observed in regular (left) and PhILM (right) images; FWHM=full width half maximum.

FIG. 6 provides a comparison between widths of axonemes observed in regular (left) and PhILM (right) images. The histogram on the left shows the intensity profile across the width of the microtubule using normal, diffraction-limited fluorescence imaging. The histogram on the right shows the distribution of localized fluorophores across the width of the microtubule in the super-resolution image.

Discussion

We disclose a new image analysis algorithm for creating super-resolution images from images with high densities of fluorophores. The invention creates microscopy images that are 5 or more times better resolution than standard microscopy images. It processes a movie in which the fluorescent molecules or particles (such as quantum dots) are photobleaching (no longer fluorescent) or blinking (going back and forth from fluorescent to dark states). It looks for the individual photobleaching events that can be located with high resolution (nm to tens of nanometers scale). The positions of the photobleaching or blinking events (i.e., the positions of the fluorescent molecules) are then drawn in a composite image that is at a much higher resolution than the original fluorescence movie.

One purpose of this invention is to provide a way to create super-resolution (super-resolution here means better than what is achievable based on the diffraction limit of light) images using standard lab equipment found in many biophysics or biology labs. Current super-resolution microscopy techniques require special laser setups and fluorescent molecules (such as PALM and STORM) that allow the fluorophores to be turned on and off so that only a small number of fluorophores are turned on at any time. This technique on the other hand uses standard laboratory microscope setups and allows one to use any fluorescent molecule (or quantum dot, etc.) that blinks or photobleaches to pick fluorophores out of the fluorescent background, and it can do it with thousands of fluorophores in an image. High resolution images are useful in studying biology (especially things like subcellular structures) at the very small scale.

The invention creates super-resolution images, uses any fluorescent molecule that is sufficiently bright enough to be detected by CCD cameras, works with green fluorescent protein (GFP), which is used in thousands of biology application, and uses standard laboratory equipment. The invention requires no photoswitchable fluorophores, no laser cycling equipment, no dual laser, etc.

Related methods include SHRImP, NALMS, STORM, dSTORM, or PALM. SHRImP and NALMS can localize multiple fluorophores with super resolution, but they cannot generalize it to thousands of fluorophores. STORM, dSTORM, and PALM can localize thousands of fluorophores but require special types of fluorophores that can be turned on at low density since high density fluorophores make it impossible to localize the fluorophores using their methods. The current technique can localize individual fluorophores at higher density, more like the SHRImP or NALMS approach, but it is generalized to any type of fluorescent background. The current technique does not require special photoswitchable fluorophores or laser equipment for turning the fluorophores on and off. In fact, our invention can also be used to analyze PALM, STORM, and dSTORM data with additional background that these current techniques cannot handle.

Relevant literature, in addition to that cited below, includes:

1. Gordon, M. P., T. Ha and P. R. Selvin 2004. Single-molecule high-resolution imaging with photobleaching. Proc Natl Acad Sci USA. 101, 6462-5.

2. Qu, X., D. Wu, L. Mets and N. F. Scherer 2004. Nanometer-localized multiple single-molecule fluorescence microscopy. Proc Natl Acad Sci USA. 2004 Aug. 3; 101(31):11298-303.

3. Betzig, E., G. H. Patterson, R. Sougrat, O. W. Lindwasser, S. Olenych, J. S. Bonifacino, M. W. Davidson, J. Lippincott-Schwartz and H. F. Hess 2006. Imaging intracellular fluorescent proteins at nanometer resolution. Science. 313, 1642-1645.

Literature related to the STORM technique include:

1. X. Zhuang, B. Huang, W. Wang, W. M. Bates, "Sub-diffraction limit image resolution in three dimensions", U.S. Pat Appl No. 61/008,661 (2008).

2. X. Zhuang, W. M. Bates, M. Rust, B. Huang, "Sub-diffraction limit image resolution and other imaging techniques", International Pat Appl No. PCT/US2007/017618 (2007).

3. X. Zhuang, W. M. Bates, M. Rust, B. Huang, "Sub-diffraction limit image resolution and other imaging techniques", U.S. patent application Ser. No. 12/012,524 (2006).

4. R. N. Zare, B. Huang, "Single-cell analysis systems, methods of counting molecules in a single cell, cylindrical fluorescence detection systems", U.S. patent application Ser. No. 12/004,874 (2007).

5. Heilemann, M., S. van de Linde, A. Mukherjee, and M. Sauer, Super-resolution imaging with small organic fluorophores. Angew Chem Int Ed Engl, 2009. 48(37): p. 6903-8.

6. Heilemann, M., S. van de Linde, M. Schuttpelz, R. Kasper, B. Seefeldt, A. Mukherjee, P. Tinnefeld, and M. Sauer, Subdiffraction-resolution fluorescence imaging with conventional fluorescent probes. Angew Chem Int Ed Engl, 2008. 47(33): p. 6172-6.

Literature Cited

1. Betzig, E., G. H. Patterson, R. Sougrat, O. W. Lindwasser, S. Olenych, J. S. Bonifacino, M. W. Davidson, J. Lippincott-Schwartz and H. F. Hess 2006. Imaging intracellular fluorescent proteins at nanometer resolution. Science. 313, 1642-1645.

2. Bates, M., B. Huang, G. T. Dempsey and X. Zhuang 2007. Multicolor super-resolution imaging with photo-switchable fluorescent probes. Science. 317, 1749-1753.

3. Rust, M. J., M. Bates and X. Zhuang 2006. Sub-diffraction-limit imaging by stochastic optical reconstruction microscopy (STORM). Nat Meth. 3, 793-796.

4. Heilemann, M., S. van de Linde, M. Schüttpelz, R. Kasper, B. Seefeldt, A.

Mukherjee, P. Tinnefeld and M. Sauer 2008. Subdiffraction-resolution fluorescence imaging with conventional fluorescent probes. Angewandte Chemie International Edition. 47, 6172-6176.

5. Thompson, R. E., D. R. Larson and W. W. Webb 2002. Precise nanometer localization analysis for individual fluorescent probes. Biophys J. 82, 2775-83.

6. Yildiz, A., J. N. Forkey, S. A. McKinney, T. Ha, Y. E. Goldman and P. R. Selvin 2003. Myosin V walks hand-over-hand: Single fluorophore imaging with 1.5-nm localization. Science. 300, 2061-5.

7. Hedde, P. N., J. Fuchs, F. Oswald, J. Wiedenmann and G. U. Nienhaus 2009. Online image analysis software for photoactivation localization microscopy. Nat Meth. 6, 689-690.

8. Taylor, J. R. 1997. An Introduction to Error Analysis: the Study of Uncertainties in Physical Measurements. University Science Books, Sausalito, Calif.

9. Aitken, C. E., R. A. Marshall and J. D. Puglisi 2008. An oxygen scavenging system for improvement of dye stability in single-molecule fluorescence experiments. Biophys. J. 94, 1826-1835.

10. Simonson, P. D., H. A. Deberg, P. Ge, J. K. Alexander, O. Jeyifous, W. N. Green and P. R. Selvin (submitted). Counting bungarotoxin binding sites of nicotinic acetylcholine receptors in mammalian cells with high signal-to-noise ratios. Biophysical J.

11. Warner, F. D. 1978. Cation-induced attachment of ciliary dyne in cross-bridges. J Cell Biol. 77, R19.

The foregoing examples and detailed description are offered by way of illustration and not by way of limitation. All publications and patent applications cited in this specification are herein incorporated by reference as if each individual publication or patent application were specifically and individually indicated to be incorporated by reference. The invention includes all possible combinations of embodiments recited herein as though belaboredly recited by matrices of such embodiments. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

What is claimed is:

1. A method of photobleaching and intermittency localization microscopy (PhILM), the method comprising steps:
   a) processing a movie of fluorophores transitioning between fluorescent and dark states by sequentially subtracting frame (n+1) from frame n to get frame n', frame n from frame (n−1) to get frame (n−1)', etc. to obtain a "backwards-subtracted movie" comprising frames 1', 2', . . . , (n−1)', n', (n+1)', etc.;
   b) detecting in the backwards-subtracted movie dark and bright spots, wherein bright spots correspond to transitions from fluorescing-states-to-dark-states ("photobleaching" events), and dark spots correspond to transitions from dark-states-to-fluorescing-states ("blinking" events) and storing corresponding frame numbers and positions of these photobleaching or blinking events;
   c) localizing positions of the fluorophore transition events with sub-pixel resolution; and
   d) creating a high resolution image by plotting the positions of the localized fluorophore transition events in a final image.

2. The method of claim 1 wherein the localizing step is performed by two-dimensional Gaussian fitting, Airy disc fitting, centroid fitting, fluoroBancroft algorithm, or wavelet segmentation.

3. A method of photobleaching and intermittency localization microscopy (PhILM), the method comprising steps:
   a) processing a movie of fluorophores transitioning between fluorescent and dark states by sequentially subtracting frame (n−1) from frame n to get frame n', frame n from frame (n+1) to get frame (n+1)', etc. to obtain a "forward-subtracted movie" comprising frames 1', 2', . . . , (n−1)', n', (n+1)', etc.;
   b) detecting in the forward-subtracted movie dark and bright spots, where in dark spots correspond to transitions from fluorescing-states-to-dark-states ("photobleaching" events), and bright spots correspond to transitions from dark-states-to-fluorescing-states ("blinking" events) and storing corresponding frame numbers and positions of these photobleaching or blinking events;
   c) localizing positions of the fluorophore transition events with sub-pixel resolution; and
   d) creating a high resolution image by plotting the positions of the localized fluorophore transition events in a final image.

4. The method of claim 3 wherein the localizing step is performed by two-dimensional Gaussian fitting, Airy disc fitting, centroid fitting, fluoroBancroft algorithm, or wavelet segmentation.

5. A method of photobleaching and intermittency localization microscopy (PhILM"), the method comprising steps:
   a) processing a movie of fluorophores transitioning between fluorescent and dark states by sequentially subtracting frame (n+1) from frame n to get frame n', frame n from frame (n−1) to get frame (n−1)', etc. to obtain a "backwards-subtracted movie" comprising frames 1', 2', . . . , (n−1)', n', (n+1)', etc.;
   b) detecting in the backwards-subtracted movie dark and bright spots using a spot detection algorithm, wherein bright spots correspond to transitions from fluorescing-states-to-dark-states ("photobleaching" events), and dark spots correspond to transitions from dark-states-to-fluorescing-states ("blinking" events) and storing corresponding frame numbers and positions of these photobleaching or blinking events;
   c) calculating a maximum number of frames that can be averaged before a transition event and after a transition event, for each spot, by comparing the spot's position and frame number with the other spots' positions and frame numbers to obtain frame ranges, wherein consecutive frames before and after the event are averaged as long as another event does not occur within a certain minimum radius of the event of interest, within the frames to be averaged;

d) averaging frames before each spot using the frame ranges calculated in step c) to produce a "pre-event averaged image" and averaging frames after each spot using the frame ranges calculated in step c) to produce a "post-event averaged image";

e) subtracting for each photobleaching event the post-event averaged image from the pre-event averaged image to produce a corresponding "fitting image", or subtracting for each blinking event the pre-event averaged image from the post-event averaged image to produce a corresponding "fitting image";

f) localizing in the fitting image positions of the fluorophore transition events with sub-pixel resolution to find the best estimate of the position of the center of the fluorophore; and g) creating from the best estimates of the positions of the fluorophores calculated in step f) a high resolution image by plotting the positions of all the localized fluorophore transition events in a final image, wherein events that are not fit by a Gaussian function in step f) are not plotted in the final image.

6. The method of claim 5 wherein the localizing step is performed by two-dimensional Gaussian fitting, Airy disc fitting, centroid fitting, fluoroBancroft algorithm, or wavelet segmentation.

7. The method of claim 5 wherein the localizing step is performed by fitting the fitting image for each photobleaching or blinking event to a two-dimensional Gaussian function, using the pixels within a determined radius of the photobleaching or blinking event, to find the best estimate of the position of the center of the fluorophore.

8. A method of photobleaching and intermittency localization microscopy (PhILM"), the method comprising steps:

a) processing a movie of fluorophores transitioning between fluorescent and dark states by sequentially subtracting frame (n−1) from frame n to get frame n', frame n from frame (n+1) to get frame (n+1)', etc. to obtain a "forward-subtracted movie" comprising frames 1', 2', . . . , (n−1)', n', (n+1)', etc.;

b) detecting in the forward-subtracted movie dark and bright spots using a spot detection algorithm, wherein dark spots correspond to transitions from fluorescing-states-to-dark-states ("photobleaching" events), and bright spots correspond to transitions from dark-states-to-fluorescing-states ("blinking" events) and storing corresponding frame numbers and positions of these photobleaching or blinking events;

c) calculating a maximum number of frames that can be averaged before a transition event and after a transition event, for each spot, by comparing the spot's position and frame number with the other spots' positions and frame numbers to obtain frame ranges, wherein consecutive frames before and after the event are averaged as long as another event does not occur within a certain minimum radius of the event of interest, within the frames to be averaged;

d) averaging frames before each spot using the frame ranges calculated in step c) to produce a "pre-event averaged image" and averaging frames after each spot using the frame ranges calculated in step c) to produce a "post-event averaged image";

e) subtracting for each photobleaching event the post-event averaged image from the pre-event averaged image to produce a corresponding "fitting image", or subtracting for each blinking event the pre-event averaged image from the post-event averaged image to produce a corresponding "fitting image";

f) localizing in the fitting image positions of the fluorophore transition events with sub-pixel resolution to find the best estimate of the position of the center of the fluorophore; and g) creating from the best estimates of the positions of the fluorophores calculated in step f) a high resolution image by plotting the positions of all the localized fluorophore transition events in a final image, wherein events that are not fit by a Gaussian function in step f) are not plotted in the final image.

9. The method of claim 8 wherein the localizing step is performed by two-dimensional Gaussian fitting, Airy disc fitting, centroid fitting, fluoroBancroft algorithm, or wavelet segmentation.

10. The method of claim 8 wherein the localizing step is performed by fitting the fitting image for each photobleaching or blinking event to a two-dimensional Gaussian function, using the pixels within a determined radius of the photobleaching or blinking event, to find the best estimate of the position of the center of the fluorophore.

* * * * *